(12) United States Patent
Javitt

(10) Patent No.: US 11,576,911 B2
(45) Date of Patent: *Feb. 14, 2023

(54) COMPOSITION AND METHOD FOR TREATMENT OF DEPRESSION AND PSYCHOSIS IN HUMANS

(71) Applicant: Glytech LLC, Ft. Lee, NJ (US)

(72) Inventor: Daniel C. Javitt, Ft. Lee, NJ (US)

(73) Assignee: GLYTECH LLC, Ft. Lee, NJ (US)

( * ) Notice: Subject to any disclaimer, the term of this patent is extended or adjusted under 35 U.S.C. 154(b) by 211 days.

This patent is subject to a terminal disclaimer.

(21) Appl. No.: 16/812,382

(22) Filed: Mar. 9, 2020

(65) Prior Publication Data

US 2020/0206219 A1 Jul. 2, 2020

Related U.S. Application Data

(60) Division of application No. 15/987,932, filed on May 24, 2018, now Pat. No. 10,583,138, which is a continuation-in-part of application No. 15/650,912, filed on Jul. 16, 2017, now Pat. No. 10,660,887, which is a continuation of application No. 13/936,198, filed on Jul. 7, 2013, now Pat. No. 9,737,531.

(60) Provisional application No. 62/518,020, filed on Jun. 12, 2017, provisional application No. 61/741,114, filed on Jul. 12, 2012, provisional application No. 61/741,115, filed on Jul. 12, 2012.

(51) Int. Cl.
| | | |
|---|---|---|
| *A61K 31/06* | (2006.01) | |
| *A61K 31/496* | (2006.01) | |
| *A61K 31/135* | (2006.01) | |
| *A61K 31/138* | (2006.01) | |
| *A61K 31/381* | (2006.01) | |
| *A61K 31/42* | (2006.01) | |
| *A61K 31/4525* | (2006.01) | |
| *A61K 31/519* | (2006.01) | |
| *A61K 31/55* | (2006.01) | |
| *A61K 31/553* | (2006.01) | |
| *A61K 31/554* | (2006.01) | |
| *A61K 45/06* | (2006.01) | |
| *A61K 31/431* | (2006.01) | |
| *A61K 31/551* | (2006.01) | |

(52) U.S. Cl.
CPC ............ *A61K 31/496* (2013.01); *A61K 31/06* (2013.01); *A61K 31/135* (2013.01); *A61K 31/138* (2013.01); *A61K 31/381* (2013.01); *A61K 31/42* (2013.01); *A61K 31/431* (2013.01); *A61K 31/4525* (2013.01); *A61K 31/519* (2013.01); *A61K 31/55* (2013.01); *A61K 31/551* (2013.01); *A61K 31/553* (2013.01); *A61K 31/554* (2013.01); *A61K 45/06* (2013.01); *A61K 2300/00* (2013.01)

(58) Field of Classification Search
CPC .. A61K 31/496; A61K 31/135; A61K 31/138; A61K 31/381; A61K 31/42; A61K 31/431; A61K 31/4525; A61K 31/519; A61K 31/55; A61K 31/551; A61K 31/554; A61K 45/06

See application file for complete search history.

(56) References Cited

U.S. PATENT DOCUMENTS

| | | |
|---|---|---|
| 6,228,875 B1 | 5/2001 | Tsai et al. |
| 9,650,352 B2 | 5/2017 | Wainer et al. |
| 2004/0157926 A1* | 8/2004 | Heresco-Levy ........ A61P 13/06 514/561 |
| 2005/0261340 A1 | 11/2005 | Weiner |
| 2006/0204486 A1 | 9/2006 | Pyke et al. |
| 2008/0194631 A1 | 8/2008 | Trovero et al. |
| 2008/0194698 A1 | 8/2008 | Hermanussen et al. |
| 2010/0069399 A1 | 3/2010 | Gant |
| 2010/0216805 A1* | 8/2010 | Barlow ................. A61K 31/357 514/249 |
| 2011/0207776 A1 | 8/2011 | Buntinx |
| 2011/0237602 A1 | 9/2011 | Meltzer |
| 2011/0306586 A1 | 12/2011 | Khan |
| 2012/0041026 A1 | 2/2012 | Waizumi |

FOREIGN PATENT DOCUMENTS

| | | |
|---|---|---|
| CN | 101090721 | 12/2007 |
| EP | 2200610 | 1/2018 |
| KR | 2007 0017136 | 2/2007 |
| WO | 2005/065308 | 7/2005 |
| WO | 2005/079756 | 9/2005 |
| WO | 2011044089 | 4/2011 |
| WO | 2012/104852 | 8/2012 |

(Continued)

OTHER PUBLICATIONS

Ceglia et al., "The 5-HT2A receptor antagonist M100,907 prevents extracellular glutamate rising in response to NMDA receptor blockade in the mPFC," Journal of Neurochemistry, 2004, 91, 189-199.

(Continued)

*Primary Examiner* — Jared Barsky

(74) *Attorney, Agent, or Firm* — JMB Davis Ben-David

(57) ABSTRACT

This application relates to combination compositions for use in treatment of depression, and which can alleviate the anxiogenic side effects of certain antidepressant and antipsychotic medications. Methods for treatment of depression and medicament side effects, particular anxiety, akathisia, and associated suicidality are also described herein.

9 Claims, 3 Drawing Sheets

(56) References Cited

FOREIGN PATENT DOCUMENTS

| WO | 2005/000216 | 9/2013 |
|---|---|---|
| WO | 2013138322 | 9/2013 |

OTHER PUBLICATIONS

Mony et al., "Identification of a novel NR2B-selective NMDA receptor antagonist using a virtual screening approach," Bioorganic & Medicinal Chemistry Letters 20(2010) 5552-5558.

Rogoz, Z. et al. "Synergistic effect of uncompetitive NMDA receptor antagonists and antidepressant drugs in the forced swimming test in rats" Neuropharmacology, Pergamon Press, Oxford, GB, 42(8): 1024-1030, (Jun. 2002).

Heresco-Levy, U. et al. "Controlled trial of d-cycloserine adjuvant therapy for treatment-resistant major depressive disorder" Journal of Affective Disorders, Elsevier Biochemical Press, Amsterdam, NL, 93(1-3): 239-243, (Jul. 2006).

Crane, G.E. "Cycloserine as an antidepressant agent" American journal of Psychiatry, American Psychiatric Publishing, Inc., US, 115(11): 1025-1026, (May 1, 1959).

Oliver et al. "Quetiapine augmentation in depressed patients with partial response to antidepressants" Human Psychopharm Clin Exp, 23:653-660, 2008.

Poleszak et al "A complex interaction between glycine/NMDA receptors and serotonergic/noradrenergic antidepressants in the forced swim test in mice" Journal of Neural Transmission, 118:1535-1546, 2011.

Ishibashi et al "Pharmacological Profile of Lurasidone, a Novel Antipsychotic Agent with Potent 5-Hydroxytryptamine 7 (5-HT7) and 5-HT1A Receptor Activity" Journal of Pharmacology and Experimental Therapeutics, 334: 171-181, 2010.

Marek et al, "The Selective 5-HT2A Receptor Antagonist M100907 Enhances Antidepressant-Like Behavioral Effects of the SSRI Fluoxetine" Neuropsychopharmacology 30: 2205-2215, 2005.

Letter to Dr. Daniel Javitt from Dr. Yehezkel Caine, CEO of Herzog Hospital, Apr. 12, 2017 (redacted) (1 page).

Letter to Dr. Yehezkel Caine, CEO of Herzog Hospital from Dr. Daniel Javitt, May 15, 2017 (redacted).

Ardayfio et al., J. Pharm and Exp Ther, 327:891-897, 2008.

Gaisler-Salomon et al., Psychopharm 196:255-267, 2008.

Carlsson et al., J. Neuraltrans. 106:123-129, 1999.

De Paulis, Curr Opin in Invest Drugs 2:123-132, 2001.

Fenton, "Depression, Suicide and Suicide Prevention in Schizophrenia," American Foundation for Suicide Prevention Education section, http://www.afsp.org/education/fenton.htm (date accessed-Dec. 3, 2015).

Jamison, "Suicide and bipolar disorder," J Clin Psychiatry. 2000;61 Suppl 9:47-51.

* cited by examiner

COMPOSITION AND METHOD FOR TREATMENT OF DEPRESSION AND PSYCHOSIS IN HUMANS

CROSS REFERENCE TO RELATED APPLICATIONS

This is a Divisional of U.S. patent application Ser. No. 15/987,932, filed May 24, 2018, which is a Continuation-in-Part of U.S. patent application Ser. No. 15/650,912, filed Jul. 16, 2017, which is a Continuation of U.S. patent application Ser. No. 13/936,198, filed Jul. 7, 2013, now issued as U.S. Pat. No. 9,737,531, which in turn claimed priority to U.S. Provisional Patent Application Nos. 61/741,114 and 61/741,115, both of which filed on Jul. 12, 2012. Benefit is additionally claimed to U.S. Provisional Patent Application No. 62/518,020, filed Jun. 12, 2017. The contents of the foregoing patent applications are incorporated by reference herein in their entirety.

FIELD

This application relates to combination compositions for use in treatment of depression, and which can simultaneously alleviate the anxiogenic side effects of certain antidepressant and antipsychotic medications, thereby enabling continued antidepressant and antipsychotic treatment. Methods for treatment of depression while simultaneously reducing medicament side effects, particularly anxiety, akathisia, and associated suicidality are also described herein.

BACKGROUND

Schizophrenia is a clinical syndrome associated with psychotic symptoms such as delusions and hallucinations, as well as a decline in function in such areas as work, social relation or self-care.

Diagnosis of schizophrenia may be determined using standard textbooks of the art, such as the Diagnostic and Statistical Manual of Mental Disorders-fifth edition (DSM-5) published by the American Psychiatric Association. Symptoms of schizophrenia are typically measured using rating scales such as the Positive and Negative Syndrome Scale (PANSS).

Symptoms of schizophrenia are treated with antipsychotic medications, which function primarily by blocking dopamine D2 receptors.

Major depression is a clinical syndrome that includes a persistent sad mood or loss of interest in activities, which persists for at least two weeks in the absence of treatment. Symptoms of major depression are typically measured using rating scales such as the Hamilton Depression Rating Scale (HAM-D) or the Beck Depression Inventory (BDI). In addition to including symptoms relevant to depressed mood, the HAM-D also contains symptoms sensitive to psychosis, including items for guilt, depersonalization/derealization and paranoia. Major depression may also be associated with symptoms of anxiety, which may be measured with rating scales such as the Hamilton Rating Scale for Anxiety (HAM-A). Depressive disorders are divided in major depression (MDD) and bipolar depression (BPD), which may be diagnosed using criteria set forth in the Diagnostic and Statistical Manual, 5th edition, published by the American Psychiatric Association (DSM-5), which provides as well additional description of mental disorders. Major depression may also occur with and without melancholic features. In addition, depressive symptoms may occur in the context of anxiety disorders such as generalized anxiety disorder, dissociative disorders, personality disorders or adjustment disorders with depressed mood (DSM-5).

5-HT2A receptors are a type of receptor for the neurotransmitter serotonin (5-HT). 5-HT2A antagonists are compounds that inhibit effects of agonists such as serotonin on 5-HT2A receptors. Selective 5-HT2A receptor antagonists and inverse agonists are presently under development for treatment of both depression and psychosis and are viewed as potential antidepressant/antipsychotic agents.

N-methyl-D-aspartate receptors (NMDAR) are a type of receptor for the brain neurotransmitter glutamate. NMDAR participate in a range of brain functions including sensory processing, cognition, and emotion regulation.

NMDAR are comprised of multiple subunits termed GluN1, GluN2 and GluN3 (formerly NR1, NR2, NR3). Multiple forms of GluN1, GluN2 and GluN3 exist. In particular, GluN2 subunits are divided into GluN2A-D subforms, which are also termed NR2A-D subunits. NMDAR may consist of various combinations of GluN1, GluN2 and GluN3 subunits in various amounts. Agonists and antagonists may affect all NMDAR equivalently, or may be selective for NMDAR containing specific subunit types.

NMDAR contain binding sites for both the neurotransmitter glutamate and for the endogenous modulatory amino acids glycine and D-serine. The glutamate binding site also selectively binds the synthetic glutamate derivative N-methyl-D-aspartate with high affinity. This site is alternately referred to as the glutamate recognition site of the NMDA recognition site of the NMDAR.

The glycine/D-serine binding site has been referred to as the glycine modulatory site, the allosteric modulatory site or the glycine-B receptor. NMDAR form an ion channel that is blocked by several drugs of abuse, such as phencyclidine (PCP), ketamine or dizocilpine (MK-801). These compounds bind to a site that has been termed the PCP receptor. Agents that block the NMDAR-associated ion channel are collectively termed noncompetitive NMDAR antagonists, or NMDAR channel blockers. Blockade of NMDAR by channel blockers leads to a clinical psychotic state that closely resembles schizophrenia.

NMDAR may also be inhibited by antagonists that bind to the glutamate recognition site, the glycine recognition site, or the channel binding site.

NMDAR may also be inhibited by antagonists that bind to the glycine recognition site. Antagonists at the glycine recognition site may be full antagonists, which monotonically reduce NMDAR activity with increasing doses, or partial agonists (mixed agonists/antagonists), which differentially affect NMDAR function within different dose ranges. In specific, partial agonists may serve as agonists at lower doses, and as antagonists at higher doses.

D-cycloserine is a compound that acts as a partial glycine-site antagonist. Levels of D-cycloserine in blood (e.g. plasma or serum) can be assessed using standard chromatographic results including without limitation high performance liquid chromatography (HPLC). D-cycloserine levels, in general, are equivalent whether serum or plasma are used for determination.

In general, D-cycloserine has net agonist effects at doses that produce blood concentrations below 10 microgram/mL, and net antagonist effects at doses that produce concentrations above 25 microgram/mL. In general, human doses at which D-cycloserine serves as an agonist are in the range of 10-100 mg/day. In general, human doses significantly in excess of 500 mg/d (e.g. 700 mg/d for an average adult of 70 kg) are needed to achieve sustained blood levels exceeding 25 microgram/mL.

Treatment-refractory depression refers to a form of depression that responds poorly to currently available treatments (e g, nimh.nih.gov/trials/practical/stard/index.shtml June 2011) and which may have different underlying etiopathological mechanisms compared with other forms of depression. Combinations of antidepressants have not been shown to be superior to monotherapy for refractory depression and typically increase risk of side effects, and so are not recommended.

Current treatments for major depression consist primarily of older antidepressants, such as monoamine oxidase inhibitors (MAOI) and tricyclic antidepressants (TCAs) (e.g. imipramine, amitryptiline, desipramine, clomipramine) that were first developed in the 1960's, and newer agents such as tetracyclic antidepressants (TeCAs), e.g. amoxapine, setiptiline, maprotiline, mianserin, mirtazapine), serotonin (SSRI) and serotonin/norephinephrine (SNRI) reuptake inhibitors (e.g., fluoxetine, fluvoxamine, paroxetine, citalopram, escitalopram, duloxetine, venlafaxine, dapoxetine, indalpine, valozodone). These agents work by modulating brain levels of monoamines, in particular norepinephrine and serotonin, and/or by blocking 5-HT2A receptors. MAOIs and TCAs are considered "broader spectrum" agents than SSRIs/SNRIs that were developed subsequently MAOI, TCAs, TeCAs, SSRIs, and SNRIs may collectively be considered traditional antidepressants.

Antipsychotics may also be effective in treatment of depression. Potentially beneficial antipsychotic medications include but are not limited to risperidone, olanzapine, quetiapine, quetiapine XR, aripiprazole, clozapine, iloperidone, sertindole, asenapine, lurasidone, cariprazine and brexpiprazole.

Despite the wide range of pharmacological options, current treatment approaches for schizophrenia and depression have severe limitations. Only 60-65% of patients respond to the initial treatment regimen and among those responding, less than half either reach remission or become symptom-free. Individuals not responding to a first course of antidepressant treatment are often switched to a different drug, with results that are generally modest and incremental.

Additionally, risk for suicide is significantly increased in depressive disorders, but may respond differentially to medication versus depressive symptoms as a whole. When suicide occurs, it is often accompanied by feelings of worthlessness or inappropriate guilt, as well as recurrent thoughts of death or suicidal ideation and guilt is an accepted proxy for suicide. While the risk of suicide increases in subjects with a depressive disorder, medications used to date to typically treat depressive disorders paradoxically increase suicidal tendencies.

A major limitation in use of antipsychotic and antidepressant medications is the liability to produce behavioral side effects, especially anxiety, agitation, and akathisia, all of which are associated with generating or exacerbating suicidality in psychotic or depressed patients. These behavioral side effects can be differentiated from symptoms of the illness by consideration of both time course and specific patterns of symptoms. In addition to akathisia, antipsychotics also produce extrapyramidal symptoms such as stiffness, tremor or dyskinesia. Akathisia, however, is differentiated from extrapyramidal symptoms and shows differential treatment response. At present, there are no approved treatments for antipsychotic-induced akathisia.

Use of antidepressants is also limited by liability to produce anxiety, agitation, and akathisia.

Limitations of antidepressants are summarized in a "black box" warning required by the FDA, as follows: "The following symptoms, anxiety, agitation, panic attacks, insomnia, irritability, hostility, aggressiveness, impulsivity, akathisia (psychomotor restlessness), hypomania, and mania have been reported in adult and pediatric patients being treated with antidepressants for major depressive disorder as well as for other indications, both psychiatric and non-psychiatric. Although a causal link between the emergence of such symptoms and either the worsening of depression and/or the emergence of suicidal impulses has not been established, there is concern that such symptoms may represent precursors to emerging suicidality" (Trivedi et al., J Clin Psychiatry, 72:765-774, 2011).

As with antipsychotic-induced akathisia, there are at present no approved treatments for antidepressant induced anxiety, agitation, or akathisia.

SUMMARY

The present invention is directed towards compositions for the treatment of depression and psychoses in humans. More particularly, the invention is directed to formulations containing antipsychotic and/or antidepressant medications including selective 5-HT2A receptor antagonists/inverse agonists and/or atypical antipsychotic medications that target both D2 and 5-HT2A receptors (serotonin-dopamine antagonists, "SDA"), and which also contain a competitive NMDAR antagonist. The present invention is also directed to methods for the treatment of humans suffering from depression and other psychoses, including, schizophrenia, by administration of the inventive compositions in antidepression and/or antipsychotic effective amounts.

In one embodiment, this invention provides an oral or parenteral dosage regimen consisting essentially of two therapeutic agents, wherein one of said two active ingredients is an antidepressant or antipsychotic agent, and the other agent consists of an NMDAR receptor antagonist.

In some embodiments of the invention, the first compound consists of a typical or atypical antipsychotic agent, though it will be appreciated that "first" and "second" can be reversed in particular embodiments in which the "first" compound is the NMDAR receptor antagonist, and the "second" compound is an antidepressant or antipsychotic agent.

In some embodiments of the invention, the first therapeutic agent is drawn from a list that includes amisulpride, aripiprazole, asenapine, bioanserin, bifeprunox, cariprazine, clotiapine, clozapine, iloperidone, lumatoperone (ITI-007), MIN-101, lurasidone, mosapromine, olanzapine, paliperidone, perospirone, quetiapine, remoxipride, risperidone, sertindole, sulpiride, ziprasidone, zotepine In some embodiments, the first therapeutic agent comprises a tetracyclic antidepressant (TeCA), selective serotonin reuptake inhibitor (SSRI), a serotonin/norephinephrine reuptake inhibitor (SNRI) a 5-HT2A antagonist/inverse agonist an atypical antidepressant with mixed agonist/antagonist activity or a combination thereof.

5-HT2A receptor antagonists/inverse agonists may be drawn from a list that includes volinanserin (MDL100,907, also known as M100907) pruvanserin (EMD281014), eplivanserin (SR-46,349), CYR-101 and pimavanserin (ACP-103).

NMDAR antagonists may be drawn from antagonists at the glycine, glutamate or polyamine recognition sites.

NMDAR antagonists may be non-selective antagonists or selective antagonists at NMDAR containing specific subunits such as the NR2A or NR2B subunits.

In some embodiments of the invention, the first therapeutic agent is drawn from a list that includes agomelatine, F2695, IEP-227162, LuAA24530, SEP-225289, LY12624803, HY10275, TIK-301/LY156735, Lonasen, LU-31-130, SLV313, Edivoxetine, OPC-34712, lisdexamfetamine, sacomeline, clouracetam, and BMS-82036.

In some embodiments, the second therapeutic agent is drawn from a list that includes ketamine, dextromethorphan, CNS-1102, AZD6765, or CGS-19755.

In a preferred embodiment of the invention, the second therapeutic agent consists of D-cycloserine, administered at a NMDAR antagonist dosage of greater than 500 mg per day but less than 1000 mg per day, and which in particular embodiments is a dosage equal to or in in excess of of 10 mg/kg (in excess of 700 mg per day for an average adult).

In some embodiments, the NMDAR antagonists consists of D-cycloserine, administered at a dose that produces peak blood levels in excess of 25 microgram/mL, but less than 125 microgram/mL.

In some embodiments, the NMDAR antagonists consists of D-cycloserine, administered at a dose that produces sustained blood levels in excess of 25 microgram/mL, but less than 125 microgram/mL. In some embodiments, these levels are sustained for a duration of 12 hours following D-cycloserine administration.

In some embodiments, this invention provides a method for treatment of a psychosis in a subject in need thereof, said method comprising providing said subject with an oral or parenteral dosage regimen as herein described.

In some embodiments this invention provides a method for treatment of depression in a subject in need thereof, said method comprising providing said subject with an oral or parenteral dosage regimen as herein described In some embodiments, the subject suffers from mania, or in some embodiments, the subject suffers from bipolar disorder.

In some embodiments, this invention provides a method for treating symptoms of autism in a subject in need thereof, said method comprising providing said subject with an oral or parenteral dosage regimen as herein described.

In some embodiments, the invention provides a method for reducing side effects associated with antipsychotic medications to a subject in need of such treatment, said method comprising providing said subject with an oral or parenteral dosage regimen as herein described.

In some embodiments, this invention provides a method for reducing side effects associated with antidepressant medications to a subject in need of such treatment, said method comprising providing said subject with an oral or parenteral dosage regimen as herein described.

In some embodiments, this invention provides a method for reducing side effects associated with NMDAR antagonist medications to a subject in need of such treatment, said method comprising providing said subject with an oral or parenteral dosage regimen as herein described.

In some embodiments, a gelling agent such as hydroxypropyl methylcellulose, together with one or more pharmaceutically acceptable excipients is used for manufacture of the sustained release agent.

In some embodiments, the sustained release formulation comprises a hydrophilic matrix comprising a gelling agent, preferably hydroxypropyl methylcellulose, an NMDAR antagonist, an antidepressant and pharmaceutically acceptable salts thereof, together with one or more pharmaceutically acceptable excipients.

In some embodiments, the sustained release formulation reduces gastric degradation of the NMDAR antagonist or the antidepressant agent by protecting the NMDAR antagonist from hydrolysis.

In some embodiments, a covalent modification is made to D-cycloserine to reduce its susceptibility to hydrolysis and gastric degradation. In some embodiments, the covalent modification creates a prodrug that is resistant to hydrolysis and gastric degradation. In some embodiments, the covalent modification is made to the primary amine group of D-cycloserine. In some embodiments, the covalent modification is made to the secondary amide group of the D-cycloserine molecule. In some embodiments, the covalent modification consists of addition of a methyl group. In some embodiments, the covalent modifications consists of a fully or partially-hydrogenated polyalkyl moiety. In some embodiments, the covalent modification creates a D-cycloserine prodrug that is metabolized by the body to D-cycloserine.

In some embodiments both the NMDAR antagonist and the antidepressant or antipsychotic medication would be manufactured for sustained release in common.

In some embodiments, the NMDAR antagonist would be manufactured for sustained release, and combined with an antidepressant or antipsychotic agent.

In some embodiments, the antidepressant or antipsychotic agent would be manufactured for sustained release, and combined with an NMDAR antagonist.

In one embodiment, an NMDAR antagonist and an antidepressant or antipsychotic agent would be selected for release characteristics permitting once daily dosing of the combined medicament, and would not require separate sustained release manufacture.

The foregoing and other objects, features, and advantages will become more apparent from the following detailed description.

DETAILED DESCRIPTION

I. Terms

Figure 1:
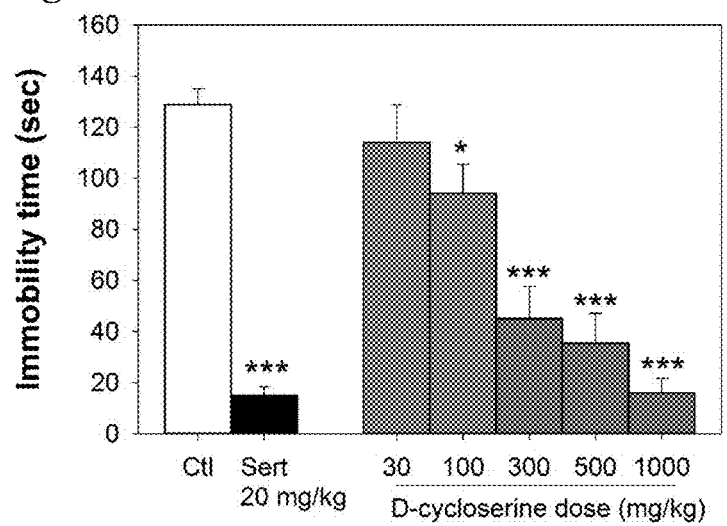
FIG. 1 shows the effects of D-cycloserine (DCS) on immobility time in the forced swim test (FST) following oral (PO) administration. Between 10 and 50 mice were treated with either control (vehicle), sertraline (20 mg/kg), or D-cycloserine (30-1000 mg/kg). *$p<0.05$ vs. control. ***$p<0.001$ vs. control. The main variable used to represent immobility in this test was the total time immobile during the 6-min test period. Statistics were performed by analysis of variance (ANOVA) with Dunnett post-hoc testing vs. the control condition or by t-test as appropriate.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." "Consisting essentially of" indicates a composition, method, or process that includes only those listed features as the active or essential elements, but can include non-active elements in addition. The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

As used herein, reference to an "effective" amount or a "therapeutically effective amount" of therapeutic agents referenced herein, it is meant a nontoxic but sufficient amount of the same to provide the desired effect. In a combination therapy of the present invention, an "effective amount" of one component of the combination is the amount of that compound that is effective to provide the desired effect when used in combination with the other components of the combination. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual.

D-cycloserine, or DCS, refers to the chemical D-cycloserine (CA Index Name: 3-Isoxazolidinone, 4-amino-, (4R)-(9CI); CAS Registry No. 68-41-7), or pharmaceutically acceptable salts thereof. DCS is an FDA (United States Food and Drug Administration)-approved drug for treatment of tuberculosis, and is sold by Eli Lilly and Company under the trade name Seromycin®. DCS is a structural analog of D-alanine, and is a broad-spectrum antibiotic produced by some strains of *Streptomyces orchidaceus* and *S. garphalus.*

Treatment-refractory depression refers to a form of depression that responds poorly to currently available treatments (e.g., as described at nimh.nih.gov/trials/practical/stard/index.shtml June 2011) and which may have different underlying etiopathological mechanisms compared with other forms of depression. Combinations of antidepressants have not been shown to be superior to monotherapy for refractory depression and typically increase risk of side effects and are not recommended.

A "prodrug" is a medication or compound that, after administration, is metabolized (i.e., converted within the body) into a pharmacologically active drug. Inactive prodrugs are pharmacologically inactive medications that are metabolized into an active form within the body.

II. Compositions for Treatment of Depression and Schizophrenia With Reduced Side Effects As shown herein, D-cycloserine induces anti-depressant effects in rodents selectively at doses that produce sustained blood (e.g. serum or plasma) levels >25 microgram/mL, and that unexpectedly, NMDAR net antagonists reduce akathisia and anxiety associated with antidepressant and/or antipsychotic treatment.

In particular we show unexpectedly that D-cycloserine reduces akathisia and anxiety associated with antidepressant and/or antipsychotic treatment when given at doses that produce sustained blood D-cycloserine concentrations >25 microgram/mL. Here we also show unexpectedly that D-cycloserine does not reduce akathisia or anxiety associated with antidepressant and/or antipsychotic treatment when given at doses that produce sustained D-cycloserine concentration below 25 micrograms/mL.

As discussed herein it was also unexpectedly observed that antidepressants prevent psychotic symptoms associated with NMDAR agonist usage.

Moreover, we show unexpectedly that manipulations reducing gastric degradation of D-cycloserine may lead to increased blood levels relative to the dose administered.

In view of these and other observations, described herein are pharmaceutical compositions that can be used in the treatment of depression and schizophrenia, and which have reduced anxiogenic side effects. The reduced anxiogenic side effects allow a patient to be provided or maintained on treatments for depression and schizophrenia (psychosis) that were not formerly possible due to the described detrimental side effects. In some embodiments the compositions are provided in oral, parenteral, or intravenous dosage regimens, which are useful in the treatment of schizophrenia or depression in a subject in need thereof, or in the reduction of the incidence or akathisia or anxiety in a subject or population in need thereof.

In a particular embodiment, the pharmaceutical compositions include a net NMDAR-antagonist effective amount of D-cycloserine; and an effective amount of an atypical antipsychotic that is a combined dopamine D2/5-HT2A receptor antagonist, wherein the NMDAR-antagonist effective amount of D-cycloserine is sufficient to produce sustained blood concentration in excess of 25 microgram/mL but lower than 125 microgram/mL.

In some embodiments, the described compositions provide an oral or parenteral dosage regimen consisting essentially of two active ingredients, wherein a first of said ingredients is an antipsychotic or antidepressant agent, and the second active ingredient is an NMDAR receptor antagonist. In some embodiments, according to this aspect, the first therapeutic agent comprises any such agent as herein described, for example, a tetracyclic antidepressant (TeCA), selective serotonin reuptake inhibitor (SSRI), a serotonin/norephinephrine reuptake inhibitor (SNRI), a selective 5-HT2A receptor antagonist, a selective 5-HT2A receptor inverse agonist, an atypical antidepressant, or an antipsychotic approved for use in treatment of depression or a combination thereof.

N-methyl-D-aspartate receptors (NMDAR) are a type of receptor for the brain neurotransmitter glutamate. NMDAR participate in a range of brain functions including sensory processing, cognition, and emotion regulation.

NMDAR are comprised of multiple subunits termed GluN1, GluN2 and GluN3 (formerly NR1, NR2, NR3). Multiple forms of GluN1, GluN2 and GluN3 exist. In particular, GluN2 subunits are divided into GluN2A-D subforms, which are also termed NR2A-D subunits. NMDAR may consist of various combinations of GluN1, GluN2 and GluN3 subunits in various amounts. Agonists and antagonists may affect all NMDAR equivalently, or may be selective for NMDAR containing specific subunit types.

NMDAR contain binding sites for both the neurotransmitter glutamate and for the endogenous modulatory amino acids glycine and D-serine.

The glutamate binding site also selectively binds the synthetic glutamate derivative N-methyl-D-aspartate with high affinity. This site is alternately referred to as the glutamate recognition site of the NMDA recognition site of the NMDAR.

The glycine/D-serine binding site has been referred to as the glycine modulatory site, the allosteric modulatory site or the glycine-B receptor.

NMDAR form an ion channel that is blocked by several drugs of abuse, such as phencyclidine (PCP), ketamine or dizocilpine (MK-801). These compounds bind to a site that has been termed the PCP receptor. Agents that block the NMDAR-associated ion channel are collectively termed non-competitive NMDAR antagonists, or NMDAR channel blockers. Blockade of NMDAR by channel blockers leads to a clinical psychotic state that closely resembles schizophrenia.

Other compounds that block NMDAR via the channel site include AZD6765 (AstraZeneca)

Other NMDAR antagonists are described in U.S. Patent appl. No. 20110306586 published Dec. 15, 2011, which is herein incorporated by reference in its entirety.

Low affinity NMDAR antagonists, such as memantine, may be distinguished from high affinity antagonists such as PCP, ketamine or dizocilpine. In general, low affinity NMDAR antagonists do not induce schizophrenia-like psychosis or PCP-like behavioral effects in rodents.

NMDAR may also be inhibited by antagonists that bind to the glutamate recognition sites, the glycine recognition site, or the polyamine (redox sensitive) binding site.

Agents that block binding of the endogenous amino acids glutamate or glycine to their respective binding sites and which have no intrinsic activity are termed competitive glutamate or glycine site antagonists. Agents which bind to these sites but which have intrinsic activity lower the endogenous ligands are termed partial agonists or mixed agonists or antagonists.

Selfotel (CGS19755) is an example of an antagonist that binds to the glutamate recognition site. Several such compounds were developed for CNS indications such as stroke or epilepsy. When used at doses sufficient to significantly inhibit NMDAR, these compounds, like channel blockers, lead to clinical psychotomimetic symptoms.

Additional compounds that functions as antagonists of the glutamate recognition site include aptiganel (Cerestat, CNS-1102) and related compounds as described in Reddy et al., J Med Chem 37:260-7. 1994.

Additional compounds that function as antagonists of the glutamate recognition site include alpha.-amino-carboxylic acid and phosphonic acid functionalities separated by a variety of spacer units. An unembellished example is 2-amino-5-phosphonovaleric acid (AP5) (Watkins, J. C.; Evans, R. H., Annu. Rev. Pharmacol. Toxicol. 1981, 21, 165), which contains a saturated carbon chain. More complex examples, which contain elements enhancing structural rigidity and therefore potency, include CPP, cis-4-(phosphonomethyl)-2-piperidinecarboxylic acid (CGS-19755) (Lehman, J. et al., J. Pharmacol. Exp. Ther. 1988, 246, 65), and (E)-2-amino-4-methyl-5-phosphono-3-pentenoic acid (CGP-37849) (Schmutz, M. et al., Abs. Soc. Neurosci. 1988, 14, 864). See U.S. Pat. No. 7,345,032, issued Mar. 18, 2008 and U.S. Pat. No. 5,168,103, incorporated herein by reference in its entirety.

Non-limiting examples of NMDAR antagonists for use in the described compositions and methods include ketamine, Selfotel, aptiganel, CPP, CGP-37849, felbamate, Gavestinel N-(6,7-dichloro-2,3-dioxo-1,2,3,4-tetrahydro-quinoxalin-5-yl)-N-(2-hydroxy-ethyl)-methanesulfonamide and 6,7-dichloro-5-[3-methoxymethyl-5-(1-oxypyridin-3-yl)-[1,2,4]triazol-4-yl]-1,4-dihydro-quinoxa-line-2,3-dione, 4-(3-phosphono-propyl)-piperazine-2-carboxylic acid (CPP), D-(E)-4-(3-phosphonoprop-2-enyl)piperazine-2-carboxylic acid (D-CPPene), SDZ-220581, PD-134705, LY-274614 and WAY-126090; quinolinic acids, such as kynurenic acid, 7-chloro-kynurenic acid, 7-chloro-thiokynurenic acid and 5,7-dichloro-kynurenic acid, prodrugs thereof, such as 4-chlorokynurenine and 3-hydroxy-kynurenine; 4-aminotetrahydrochinolin-carboxylates, such as L-689,560; 4-hydroxyquinolin-2(1H)-ones, such as L-701,324; quinoxalinediones, such as licostinel (ACEA-1021) and CGP-68,730A; 4,6-dichloro-indole-2-carboxylate derivatives such as MDL-105,519, gavestinel (GV-150,526) and GV-196,771A; tricyclic compounds, such as ZD-9,379 and MRZ-2/576, (+)-HA-966, morphinan derivatives such as dextromethorphan and dextrophan; benzomorphans, such as BIII-277CL; other opioids, such as dextropropoxyphene, ketobemidone, dextromethadone and D-morphine; amino-adamantanes, such as amantadine and memantine; amino-alkyl-cyclohexanes, such as MRZ-2/579; ifenprodil and ifenprodile-like compounds such as eliprodil and PD-196,860; iminopyrimidines; or other NMDA-antagonists such as nitroprusside, D-cycloserine, 1-aminocyclopropane-carboxylic acid, dizocilpine (MK 801) and its analogs, (R)-ketamine, (S)-ketamine, remacemide and its des-glycinyl-metabolite FPL-12,495, AR-R-15,896, methadone, sulfazocine, AN19/AVex-144, AN2/AVex-73, Besonprodil, CGX-1007, EAB-318, and NPS-1407.

NMDAR may also be inhibited by antagonists that bind to the glycine recognition site.

D-cycloserine is a compound that acts as a partial glycine-site antagonist, also termed mixed agonist/antagonist. The effects of D-cycloserine on the NMDAR are dependent on blood levels of the drug. D-cycloserine functions as a net glycine-site agonist at blood levels <10 micrograms/mL, and as a net glycine-site antagonist at blood levels >25 micrograms/mL.

D-cycloserine is commonly supplied in 250 mg capsules, permitting dosing at 250 mg, 500 mg, 750 mg or 1000 mg per day. D-cycloserine may also be administered at intermediate doses, for example, 200 mg, 300 mg, 400 mg, 500 mg, 600 mg, 700 mg, 800 mg, 850 mg, 900 mg or 950 mg per day.

In a particular embodiment, the D-cycloserine component of the described compositions is administered at a dosage of greater than 500 mg per day but less than 1000 mg per day, to produce a net NMDAR antagonist effect wherein sustained serum levels are in excess of 25 micrograms/mL, but less than 125 micrograms/mL. An exemplary dosage for providing such effective net antagonist amounts is greater or equal than 10 mg/kg/day (700 mg for an average adult of 70 kg). Particular embodiments of the described compositions include a D-cycloserine component administered at a dosage that produce sustained serum levels of 25-40 micrograms/mL, such as 26, 27, 28, 29, 30, 31, 32, 33, 34 and 35 micrograms/mL or greater.

Pharmacokinetics (PK) of D-cycloserine in humans after a dose of 500 mg have been previously studied. Critical parameters when examining the PK of a drug in blood include maximum (peak) concentration achieved (Cmax), time to maximum concentration (Tmax) and area under the curve (AUC) during the dosing interval.

For example, Zhu et al. (Zhu M, Nix D E, Adam R D, Childs J M, Peloquin C A. Pharmacokinetics of cycloserine under fasting conditions and with high-fat meal, orange juice, and antacids. Pharmacotherapy. 2001; 21(8):891-7) showed median Cmax values of 14.8 microgram/mL following administration of a single D-cycloserine dose of 500 mg under fasting conditions, with a range of 12.1-30.6 microgram/mL. Median AUC levels over 24 hr were 214 microgram-hr/mL with a range of 163-352, corresponding to median sustained plasma levels of 8.9 microgram/mL with a range of 6.8-14.7 microgram/mL.

Park et al., (Park S I, Oh J, Jang K, Yoon J, Moon S J, Park J S, Lee J H, Song J, Jang I J, Yu K S, Chung J Y. Pharmacokinetics of Second-Line Antituberculosis Drugs after Multiple Administrations in Healthy Volunteers. Antimicrob Agents Chemother. 2015; 59(8):4429-35) evaluated pharmacokinetics of 250 mg PO D-cycloserine given every 12 hrs, and observed mean Cmax values of 24.9 microgram/mL and a mean AUC over 12 hrs of 242.3 mg-h/L, corresponding to a mean plasma level of 20.2 microgram/mL.

Hung et al., 2014 (Hung W Y, Yu M C, Chiang Y C, Chang J H, Chiang C Y, Chang C C, Chuang H C, Bai K J. Serum concentrations of cycloserine and outcome of multidrug-resistant tuberculosis in Northern Taiwan. Int J Tuberc Lung Dis. 2014; 18(5):601-6) evaluated PK levels during clinical treatment with DCS. Mean dose across subjects was 8.8 mg/kg, with the majority of subjects (n=27) receiving 500 mg/day DCS, and a minority either 750 mg/d (n=4) or 250 mg/d (n=2). DCS concentrations at 2 and 6 hr after dosing were 19.7 and 18.1 microgram/mL.

Hung et al., 2014 also evaluated dosing as a function of mg/kg, and found a highly significant correlation between serum concentration and D-cycloserine dose. Based upon this relationship, a human dose exceeding 10 mg/kg is required to produce a serum level in excess of 25 microgram/mL. This dose would translate into a daily dose of 700 mg/kg for an average 70 kg individual.

Thus, a consistent finding of human D-cycloserine PK studies is that sustained blood levels following administration of D-cycloserine at a dose of 500 mg/day are consistently below 25 microgram/mL, and so would not be expected to act as a net NMDAR antagonist as required for the described compositions and methods. By extension, to achieve the net NMDAR antagonist effect required in the compositions and methods described herein (greater than 25 microgram/mL), greater than 500 mg/day DCS is required, with preferred daily doses of above 700 mg/kg for the average individual, and preferred weight-based dosing of >10 mg/kg. The described compositions can include D-cycloserine provided at a weight-based dose of between 10-25 mg/kg/day, such as but not limited to 12, 14, 15, 16, 20, 22, and 24 mg/kg/day.

In addition to the dosages described herein by the sustained blood concentration produced, the mg/kg/day, and the mg/day daily dose, dosages can also be represented in terms of molarity. Given the molecular weight of D-cycloserine as 102 g/mole, the proposed concentration of greater than 25 ug/mL corresponds to a molarity-based level of greater than 245 micromolar. As previously described, and as shown herein (see Table 4 for example), dosages below this concentration will not provide the net antagonistic effect utilized in the current compositions and methods.

The inclusion of an enteric coating is known to decrease sensitivity of medications to hydrolysis in the stomach. Reduction of hydrolysis by enteric coating would decrease the oral dose of D-cycloserine needed to achieve the desired NMDAR-antagonist blood levels of between 25 and 125, particularly between 25 and 40 microgram/mL. Therefore, in particular embodiments wherein the pharmaceutical composition includes an enteric coating, the D-cycloserine can be provided at less than 500 mg/day, such as 450, 400, 350, 300, 250 mg/day or at an even lower amount. It will be appreciated that the dosage of D-cycloserine for use in the described compositions is one that produces a net NMDAR antagonist effect, corresponding to peak and sustained blood levels of between 25 and 125 microgram/mL. Additional approaches for protecting compounds from gastric degradation are disclosed in U.S. Pat. Nos. 8,105,626, 4,853,230, 6,328,994, US appl No. 2002/0039597 and JP62-277322A, which are hereby incorporated by reference.

Felbamate is another example of a NMDAR antagonist compound that may act via the glycine binding site. When administered to humans, felbamate produces psychotic effects that limit its clinical utility (e.g. Besag F M, Expert Opin Drug Saf 3:1-8, 2004).

Gavestinel (GV-150,526) is another example of a glycine binding site antagonist. Other compounds are described in DiFabrio et al., J Med Chem 40:841-50, 1997, which is hereby incorporated by reference.

GlyX-13 (Rapastinel) is a tetra-peptide (threonine-proline-proline-threonine) that functions as a mixed agonist/antagonist at the glycine site. NRX-1074 (apostimel) is an orally available molecule with similar properties to GlyX-13. NYX-2925 ((2S, 3R)-3-hydroxy-2-((R)-5-isobutyryl-1-oxo-2,5-diazaspiro[3.4]octan-2-yl)butanamide) is a small molecule designed based on effects of GlyX-13. AGN-241751 (Allergan) is an orallly available, small molecule analog of GlyX-13. CERC-301 (Rislenemdaz) is an orally-active, selective NMDAR subunit 2B antagonist. AZD-6765 (Lanicemine) is a low-trapping NMDAR antagonist. S-ketamine (esketamine) is the S-isomer of racemic ketamine. R-ketamine is the R-isomer of racemic ketamine. AV-1.01 (4-Chlorokynurenine (4-Cl Kyn) is an orally active small molecule prodrug of 7-chlorokynurenic acid, which acts as an NMDAR glycine-site antagonist.

Other compounds effective in blocking the glycine binding site are described in U.S. patent application Ser. No. 13/440,368 filed Apr. 5, 2012 and U.S. patent application Ser. No. 14/162,328 filed Jan. 23, 2014, which are hereby incorporated by reference.

Other examples of glycine site antagonists that are suitable for use in the pharmaceutical compositions and methods of this invention are those referred to in the following: U.S. Pat. No. 6,667,317 which was issued on Dec. 23, 2003; U.S. Pat. No. 6,080,743 which was issued Jun. 27, 2000; U.S. Pat. No. 5,990,108, which was issued on Nov. 23, 1999; U.S. Pat. No. 5,942,540, which issued on Aug. 24, 1999; World Patent Application WO 99/34790 which issued on Jul. 15, 1999; WO 98/47878, which was published on Oct. 29, 1998; World Patent Application WO 98/42673, which was published on Oct. 1, 1998; European Patent Application EP 966475A1, which was published on Dec. 29, 1991; World Patent Application 98/39327, which was published on Sep. 11, 1998; World Patent Application WO 98/04556, which was published on Feb. 5, 1998; World Patent Application WO 97/37652, which was published on Oct. 16, 1997; U.S. Pat. No. 5,837,705, which was issued on Oct. 9, 1996; World Patent Application WO 97/20553, which was published on Jun. 12, 1997; U.S. Pat. No. 5,886,018, which was issued on Mar. 23, 1999; U.S. Pat. No. 5,801,183, which was issued on Sep. 1, 1998; World Patent Application WO 95/07887, which was issued on Mar. 23, 1995; U.S. Pat. No. 5,686,461, which was issued on Nov. 11, 1997; U.S. Pat. No. 5,622,952, issued Apr. 22, 1997; U.S. Pat. No. 5,614,509, which was issued on Mar. 25, 1997; U.S. Pat. No. 5,510,367, which was issued on Apr. 23, 1996; European Patent Application 517,347A1, which was published on Dec. 9, 1992; U.S. Pat. No. 5,260,324, which published on Nov. 9, 1993. The foregoing patents and patent applications are incorporated herein by reference in their entireties.

Other examples of glycine site antagonists that can be used in the pharmaceutical composition and methods of this invention are N-(6,7-dichloro-2,3-dioxo-1,2,3,4-tetrahydroquinoxalin-5-yl)-N-(2-hydroxy-ethyl)-methanesulfonamide and 6,7-dichloro-5-[3-methoxymethyl-5-(1-oxypyridin-3-yl)-[1,2,4]triazol-4-yl]-1,4-dihydro-quinoxa-line-2,3-dione.

Additional NMDAR antagonists include without being limited thereto, N-containing phosphonic acids, such as norvaline (AP5), D-norvaline (D-AP5), 4-(3-phosphonopropyl)-piperazine-2-carboxylic acid (CPP), D-(E)-4-(3-phosphonoprop-2-enyl)piperazine-2-carboxylic acid (D-CPPene), cis-4-(phosphonomethyl)-2-piperidine carboxylic acid (Selfotel, CGS 19755), SDZ-220581, PD-134705, LY-274614 and WAY-126090; quinolinic acids, such as kynurenic acid, 7-chloro-kynurenic acid, 7-chloro-thio-kynurenic acid and 5,7-dichloro-kynurenic acid, prodrugs thereof, such as 4-chlorokynurenine and 3-hydroxy-kynurenine; 4-aminotetrahydrochinolin-carboxylates, such as L-689,560; 4-hydroxyquinolin-2(1H)-ones, such as L-701, 324; quinoxalinediones, such as licostinel (ACEA-1021) and CGP-68,730A; 4,6-dichloro-indole-2-carboxylate derivatives such as MDL-105,519, gavestinel (GV-150,526) and GV-196,771A; tricyclic compounds, such as ZD-9,379 and MRZ-2/576, (+)-HA-966, morphinan derivatives such as dextromethorphan and dextrophan; benzomorphans, such as BIII-277CL; other opioids, such as dextropropoxyphene, ketobemidone, dextromethadone and D-morphine; aminoadamantanes, such as amantadine and memantine; aminoalkyl-cyclohexanes, such as MRZ-2/579; ifenprodil and ifenprodile-like compounds such as eliprodil and PD-196, 860; iminopyrimidines; or other NMDA-antagonists such as nitroprusside, D-cycloserine, 1-aminocyclopropane-carboxylic acid, dizocilpine (MK 801) and its analogs, phencyclidine (PCP), ketamine ((R,S)-2-(2-Chlorphenyl)-2-(methylamino)cyclohexan-1-on), (R)-ketamine, (S)-ketamine, remacemide and its des-glycinyl-metabolite FPL-12,495, AR-R-15,896, methadone, sulfazocine, AN19/AVex-144, AN2/AVex-73, Besonprodil, CGX-1007, EAB-318, Felbamate and NPS-1407. NMDA-Antagonists are, for example, disclosed in "Analgesics," edited by H. Buschmann, T. Christoph, E. Friderichs, C. Maul, B. Sundermann, 2002, Wiley-VCH Verlag GmbH & Co. KGaA, Weinheim, Germany, in particular pages 389-428. The respective parts of the description are hereby incorporated by reference and form part of the present disclosure.

Antagonists may be selective for the GluN2B (NR2B) containing subtype. Examples of compounds that are selective for NR2B containing receptors include ifenprodil, traxoprodil (CP-101,606), besonprodil, Ro25-6981, MK-0657 and EVT-101.

Along with identified NMDAR antagonists, additional such compounds can be identified using well-validated electrophysiological assays such as modulation of NMDA-receptor mediated responses to NMDA glutamate-site agonists, or radioreceptor assays, such as modulation of binding to the NMDA PCP-receptor channel binding site. Glycine site agonists and antagonists can also be distinguished based upon both electrophysiology and receptor binding from compounds such as phencyclidine (PCP) or ketamine that bind to the channel site. Partial agonists are defined as compounds that have reduced efficacy for inducing conformational change in receptors (typically 40-80%) relative to full agonists, and which may induce agonist effects at low dose but antagonist effects at high dose.

The NMDAR antagonist ketamine is currently approved as an anesthetic agent. It has also been reported to show beneficial effects in treatment resistant depression in small scale clinical trials. However, its utility is limited by psychotomimetic effects. The low affinity NMDAR antagonist memantine is approved for use in dementia. Otherwise, NMDAR antagonists have no established clinical utility.

In general, NMDAR antagonists are considered contraindicated for use in schizophrenia or depression. For example, the NMDAR antagonist D-cycloserine is contraindicated by FDA for use in depression, severe anxiety or psychosis. Barlow (US Patent Publication No. 2010/0216805) has proposed that D-cycloserine may be effective in treating depression, but only at concentrations of below 100 micromolar, which would correspond to plasma concentrations of under 11 microgram/mL, in which D-cycloserine is acting as a net agonist, rather than the net antagonist activity of FDA contraindications and the current invention.

Plasma levels of D-cycloserine may be assessed using standard chromatographic techniques such as but not limited to high performance liquid chromatography. In general, blood levels above 25 microgram/mL lead to increased risk in psychotomimetic effects Anti-depressant effects of psychotropic compounds may be assessed using well-established rodent behavioral assays such as the forced swim test (e.g. Cryan et al., Neuroscience and biobehavioral reviews. 29:547-69, 2005).

The compositions described herein can in certain embodiments include Antipsychotic agents. Antipsychotics may be divided into typical (e.g. chlorpromazine, haloperidol, perphenazine) vs. atypical (e.g. amisulpride, aripiprazole, asenapine, bioanserin, bifeprunox, cariprazine, clotiapine, clozapine, iloperidone, lumatoperone (ITI-007), lurasidone, mosaproamine, olanzapine, paliperidone, perospirone, quetiapine, remoxipride, risperidone, sertindole, sulpiride, ziprasidone, zotepine) based upon receptor binding, preclinical effects and side effect profile. Clinically effective doses of antipsychotic medication typically produce >60% occupancy of dopamine D2 receptors. Atypical antipsychotics may be partial or full D2 antagonists and may also have activity at additional catecholamine and serotonin receptor types, including 5-HT2A and 5-HT2C receptors and adrenergic alpha1 and alpha2 receptors. Atypical antipsychotics may also affect other receptor types, such as such as muscarinic cholinergic receptors.

Examples of antipsychotics that function as dual antagonists of D2 and 5-HT2A receptors (also known as "serotonin dopamine antagonists" or SDA) include aripiprazole, asenapine, cariprazine, clotiapine, clozapine, iloperidone, lumatoperone (ITI-007), MIN-101, lurasidone, olanzapine, paliperidone, quetiapine, remoxipride, risperidone, sertindole, ziprasidone. The relative proportion of D2 vs. 5-HT2A receptor antagonism may differ across compounds.

In a particular embodiment, the described composition includes lurasidone, which can be provided in a dose between 20-200 mg/day.

It will be appreciated that by reducing the anxiogeneic side effects of atypical antipsychotic agents, the combination compositions and treatments described herein can, in certain embodiments, allow for provision and maintenance of treatment with such agents, such as lurasidone, that was previously unavailable. For example, for certain subjects, the provision of lurasidone can induce side effects such that treatment must be discontinued. However, in the context of the current combinations with D-cycloserine, or an alternative NMDAR net antagonist compound, lurasidone treatment can be continued, or the dosage even increased without continuing or increasing the prior side effects.

Antipsychotics may also be effective in treatment of depression. Potentially beneficial antipsychotic medications include but are not limited to risperidone, olanzapine, quetiapine, quetiapine XR, aripiprazole, clozapine, iloperidone, sertindole, asenapine, lurasidone, cariprazine and brexpiprazole (OPC-34712).

Other antipsychotics and antidepressants marketed or in development include, Valdoxan (agomelatine), AGO178) (Servier, Novartis), F2695, SEP-227162 (Sepracor), LuAA24530 (tedatioxetine, Lundbeck, Takeda), SEP-225289 (Sepracor), LY12624803, HY10275 (Lilly, Hypnion), TIK-301/LY156735 (Tikvah Therapeutics), Lonasen (bioanserin, Dainippon), LU-31-130 (Lundbeck), SLV313 (Solvay), Edivoxetine (LY2216684, Lilly), OPC-34712 (Brexpiprazole, Otsuka/Lundbeck), Vyvanse (lisdexamfetamine, Shire), BCI-224 (sacomeline, BrainCells), BCI-540 (clouracetam, BrainCells), BMS-82036 (BMS/AMRI).

5-HT2A receptors are a type of receptor for the neurotransmitter serotonin (5-HT). 5-HT2A antagonists are compounds that inhibit effects of agonists such as serotonin on 5-HT2A receptors. Inverse agonists are compounds that, in addition, reduce activity below basal levels. 5-HT2A receptor antagonists can be non-selective for 5-HT2A vs. other serotonin receptors (e.g. 5-HT2C), or selective for 5-HT2A receptors. Selective 5-HT2A antagonists can be developed and characterized using standard assay procedures, such as those described in U.S. Pat. No. 7,713,995 issued on May 11, 2010, which is herein incorporated by reference in its entirety.

Agents that act as non-selective serotonin receptor antagonists include ritanserin, ketanserin, seganserin, and ICI-169369. Agents that act as selective 5-HT2A antagonists or inverse agonists include volinanserin (MDL100,907, also known as M100907) pruvanserin (EMD281014), eplivanserin (SR-46349, Citryri), CYR-101 and pimavanserin (ACP-103). Selective 5-HT2A receptor antagonists and inverse agonists are presently under development for treatment of both depression and psychosis and are viewed as potential antidepressant/antipsychotic agents.

Additional 5-HT2A receptor antagonists or inverse agonists are described in U.S. Pat. No. 7,875,632 which was issued on Jan. 25, 2011; U.S. Pat. No. 7,868,176 issued on Jan. 11, 2011; U.S. Pat. No. 7,863,296 issued on Jan. 4, 2011; U.S. Pat. No. 7,820,695 issued Oct. 26, 2010; and/or U.S. Pat. No. 7,713,995 issued May 11, 2010 which are herein incorporated by reference in its entirety.

In particular embodiments, the described compositions include an antipsychotic agent, consisting of a typical or atypical antipsychotic, which can in some embodiments be a serotonin dopamine antagonist (SDA). In some embodiments, the antipsychotic agent is selected from the group consisting of amisulpride, aripiprazole, asenapine, bioanserin, bifeprunox, brexpiprazole, cariprazine, clotiapine, clozapine, iloperidone, lurasidone, mosaproamine, olanzapine, paliperidone, perospirone, quetiapine, remoxipride, risperidone, sertindole, sulpiride, ziprasidone, zotepine.

Antipsychotics and antidepressants, including 5-HT2A receptor antagonists, may also be used therapeutically in the treatment of bipolar disorder (manic depressive psychosis), Alzheimers disease, Parkinsons disease, dementia, anxiety disorders, post-traumatic stress disorder, pain and developmental disorders including autism.

In some embodiments, the two active ingredients are provided in a single pharmaceutical composition, and in some embodiments, the invention contemplates a kit or combined dispenser packet containing each of the two active ingredients.

It is to be understood that the described compositions are provided by "co-administration" and that the co-administration of either of the two active ingredients to a subject can, in certain embodiments, be combined in a single formulation. In other embodiments, the active ingredients are provided in separate formulations, and which administration can be coincident or staggered.

The compositions described herein can be administered by a variety of well-established medicinal routes including intravenously, intraperitoneally, parentally, intramuscularly, or orally.

In some embodiments, solid compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, lipids, alginic acid, or ingredients for controlled slow release. Disintegrators that can be used include, without limitation, micro-crystalline cellulose, corn starch, sodium starch glycolate, and alginic acid. Tablet binders that may be used include without limitation, acacia, methylcellulose, sodium carboxymethylcellulose, polyvinylpyrrolidone (Povidone), hydroxypropyl methylcellulaose, sucrose, starch, and ethylcellulose.

In some embodiments, liquid compositions for oral administration prepared in water or other aqueous vehicles can include solutions, emulsions, syrups, and elixirs containing, together with the active compounds(s), wetting agents, sweeteners, coloring agents, and flavoring agents.

In other embodiments, the formulations as herein described, in particular with regard to oral formulations, are envisaged to comprise slow release tablet formulations. Such slow release tablet formulations may, for example, comprise commercially available formulations containing known anti-depressant medications, such as, for example, Effexor® or Seroquel®, both of which are already available in extended length (XR) formulations, however the formulation may be modified to further incorporate an NMDA receptor antagonist.

In other embodiments, the formulations as herein described, in particular with regard to oral formulations, are envisioned to comprise both short acting and extended release formulations.

Other compounds can be used to control release include cellulose, ethylcellulose, gelatin, hypromellose, iron oxide, and titanium oxide. In some matrix systems, drug release is controlled mainly by diffusion through matrix pores and not by the erosion at the polymers. Drug delivery can also be controlled by use of reservoir type systems in which release is controlled by osmotic gradient across the coating membrane. Capsules can be manufactured which contain granules with different microencapsulation properties which can be blended to achieve a composition that has a desired release rate.

In some embodiments, the invention contemplates employing/providing a sustained release formulation containing the agents as herein described, further comprising a gelling agent, preferably hydroxypropyl methylcellulose, and 11-[4-[2-(2-hydroxyethoxy)ethyl]-1-piperazinyl]dibenzo-[b.f][1,4]thiazepin e, or a pharmaceutically acceptable salt thereof, together with one or more pharmaceutically acceptable excipients. The term gelling agent as used herein means any substance, which forms a gel when in contact with water.

Also provided herein are methods for treating depression in a subject in need thereof, by administering an effective amount of a composition described herein in the form of an oral or parenteral dosage or a parenteral injection.

In some embodiments, the subject suffers from schizophrenia, or a depressive disorder, including major depressive disorder or bipolar depressive disorder.

In some embodiments, the invention provides a method for reducing the incidence of suicide or reducing the severity of suicide ideation and behaviors in a subject or population in need thereof, by providing the subject with an oral or parenteral or parenteral dosage regimen of a composition as herein described.

It is expected that a subject undergoing treatment with the methods and compositions described herein will experience significant improvements in depression. Relative to subjects treated with alternative treatments for depression, subjects treated accordingly will experience, in some embodiments, greater improvement, or more long-lasting improvement, as measured by any clinically recognized assessment method for depression (e.g., the 21-item Hamilton Depression Rating Scale). Similarly, a subject undergoing treatment with the described compositions and methods can experience significant improvements in anxiety. Relative to subjects treated with alternative treatments for anxiety, subjects treated accordingly will experience, in some embodiments, greater improvement, or more long-lasting improvement, as measured by any clinically recognized assessment method for anxiety (e.g., the Hamilton Anxiety Rating Scale) Likewise, a subject undergoing treatment with the described compositions and methods can experience significant improvements in akathisia. Relative to subjects treated with alternative treatments for akathisia, subjects treated accordingly will experience, in some embodiments, greater improvement, or more long-lasting improvement, as measured by any clinically recognized assessment method for akathisia (e.g., the Barnes Akathisia Rating Scale). Also, a subject undergoing treatment with the described compositions and methods can experience significant improvements in psychosis. Relative to subjects treated with alternative treatments for psychosis, subjects treated accordingly will experience, in some embodiments, greater improvement, or more long-lasting improvement, as measured by any clinically recognized assessment method for psychosis (e.g., the Positive and Negative Symptom Scale).

It should be noted that not every subject will benefit therapeutically from the described compositions and methods, just as other pharmaceutical agents do not typically benefit every patient.

The following examples are provided to illustrate certain particular features and/or embodiments. These examples should not be construed to limit the disclosure to the particular features or embodiments described.

EXAMPLES

Example 1: Effect of NMDAR Antagonists on Akathisia Induced by Selective 5-HT2A Antagonists or Atypical Antipsychotics that Function as Combined D2/5-HT2A Receptor Antagonists Background Drug induced akathisia is a common side effect of both antipsychotic and antidepressant medication and may be seen even with newer atypical antipsychotics (Iqbal et al., CNS Spectrums, 12:1-13, 2007). This syndrome has also been described as anxiety/jitteriness syndrome (Sinclair et al., Br J Psychiatry, 194:483-90, 2009), which is also seen following both SSRIs and tricyclic antidepressants.

Although no exact animal models exist at present, rodent activity measures which assess partial restlessness have been proposed to have face validity (Sachdev and Brune, Neurosci Biobehav Rd 24:269-277, 2000), justifying their use. Agonists at the 5-HT2A receptor, such as (+/−)-1-(2,5-dimethoxy-4-iodophenyl)-2-aminopropane (DOI) have well described anxiolytic properties that may be detected in rodent assays such as the four-plate test or the elevated plus maze (Nic Dhonnchadha et al, Behavioural brain research. 147:175-84, 2003). Effects of 5-HT2A ligands may be mediated in part via the GABA system (Masse et al., Behav Brain Res 177:214-26, 2007), increasing the relevance of this mechanisms for akathisia.

The present investigation tests the hypothesis that NMDAR antagonists may reverse the akathisia-induced effects of agents that work in whole or in part through 5-HT2A blockade, including selective 5-HT2A antagonists/inverse agonists, anti-depressants, and atypical antipsychotics. Given the association between suicidality, and as described herein, the reduction and/or reversal of akathisia is understood to be indicative of a reduction in suicidality and an increased suicidal tendency that may be induced by certain atypical antipsychotic medications.

Methods

All studies were performed at PsychoGenics, Inc., headquartered at 765 Old Saw Mill River Road, Tarrytown, N.Y. using an elevated plus maze (EPM) apparatus to assess behavioral effects of medication.

Preparation

Male C57Bl/6J mice from Jackson Laboratories (Bar Harbor, Me.) were used for this study. Mice were received at 6-weeks of age. Upon receipt, mice were assigned unique identification numbers (tail marked) and were group housed with 4 mice/cage in OPTI mouse ventilated cages. All animals remained housed in groups of four during the remainder of the study. All mice were acclimated to the colony room for at least 1 week prior to testing and were subsequently tested at an average of 7 weeks of age.

During the period of acclimation, mice were examined on a regular basis, handled, and weighed to assure adequate health and suitability. Animals were maintained on a 12/12 light/dark cycle; testing was performed during the light phase. The room temperature was maintained between 20 and 23° C. with a relative humidity maintained between 30% and 70%. Chow and water were provided ad libitum for the duration of the study. In each test, animals were randomly assigned across treatment groups. All animals were euthanized after the completion of the study.

Apparatus

The elevated plus maze test assessed anxiety. The maze (Kinder Scientific; Poway, Calif.) consists of two closed arms (14.5 cm h×5 cm w×35 cm 1) and two open arms (6 cm w×35 cm 1) forming a cross, with a square center platform (6×6 cm). All visible surfaces are made of black acrylic. Each arm of the maze was placed on a support column 56 cm above the floor. Antistatic black vinyl curtains (7' high) surround the EPM to make a 5' w×5' 1 enclosure. Animals were allowed to acclimate to the experimental room at least 1 hr before the test. Mice were placed in the center of the elevated plus maze facing the closed arm for a 5-min run. All animals were tested once. The time spent, distance traveled, and entries in each arm were automatically recorded by the computer. The EPM was thoroughly cleaned after each test.

Medications

Medications were administered by ip injection. All medications were dissolved in appropriate vehicle. Doses are expressed in milligrams per kilogram (mg/kg). Test compounds, as shown in Table 1, were administered 30 min before testing. In all cases, 2,5-Dimethoxy-4-iodoamphetamine (DOI) 2 mg/kg was administered 10 min before testing.

Statistical Analysis

The primary dependent measure for this study consisted of % of time spent within the open arms, which is considered a measure of anti-anxiety effects. Between-condition comparisons were performed using t-test or post-hoc Dunnett testing with two-tailed significance of $p<0.05$.

Results

Specific effects of NMDAR antagonists on anxiety/akathisia related symptoms were assessed using the measure % time in open arms, which measures willingness to enter an exposed vs. enclosed section of the EPM. Because it represents a ratio between activity in open and closed arms, it is relatively insensitive to changes in overall activity levels. Potential non-specific effects were assessed using the total distance travelled, which is a measure of overall activation.

Locomotor hyperactivity induced by NMDAR antagonists is considered a rodent model of psychosis. 5-HT2A antagonists are known to reverse effects of non-competitive NMDAR channel blockers on rodent activity, reflecting their potential use as antipsychotics. However, no studies have previously investigated the ability of competitive NMDAR antagonists acting at either the glycine or glutamate sites to reverse potential akathisia-related anxiogenic effects of high affinity 5-HT2A antagonists, or other compounds such as anti-depressants or atypical antipsychotics potentially associated with antagonism at 5-HT2A receptors.

Description of the Results

We have previously demonstrated (U.S. Pat. No. 9,846,453) that selective 5-HT2A receptor antagonists, including MDL100,907, EMD281,014 and ketanserin significantly reduced distance travelled in the open arm and % time in the open arm, suggesting a significant increase in anxiety and/or akathisia We also demonstrated that D-cycloserine at an NMDAR antagonist dose of 300 mg/kg significantly increased distance travelled in the open arm and % time in the open arms in the presence of MDL100,907, and produced numerical increases in combination with both EMD281,014. There results were also shown in combinations of D-cycloserine and the atypical antipsychotic lurasidone. The previously described data were also indicative of a potential to reduce suicidality induced by such antidepressant and atypical antipsychotic agents. The previously presented rodent data has since been supported by initial human trials (see clinicaltrials.gov, trial identification number NCT01833897).

Here, we provide additional data supporting a preferential anti-akathisia/anxiety (and therefore anti-suicidality) effect of D-cycloserine administered at high dose (300 mg/kg, i.e. at a dose producing a net NMDAR antagonist effect equivalent to above a blood concentration of 25 micrograms/mL) vs. low dose (30 mg/kg, a non-antagonist dose).

Here, we provide additional data supporting a preferential effect of competitive vs. non-competitive NMDAR antagonists in the treatment of akathisia induced by selective 5-HT2A receptor antagonists or atypical antipsychotics.

Results are shown in Table 1, and are further described below

TABLE 1

Effect of specified agents on performance in the elevated plus maze

| Line | Condition | N | Distance Traveled Open (DTO) Mean | Distance Traveled Open (DTO) Std dev | Percent open (PCT) Mean | Percent open (PCT) Std dev | Statistical effects (p values) vs. Comparator | DTO | PCT |
|---|---|---|---|---|---|---|---|---|---|
| 1 | Control | 52 | 183.3 | 87.0 | 36.5 | 15.6 | | | |
| 2 | DCS 30 mg/kg | 10 | 295.8 | 104.6 | 44.6 | 10.6 | control | 0.001 | 0.121 |
| 3 | DCS 300 mg/kg | 20 | 287.5 | 143.3 | 45.4 | 16.7 | control | <0.001 | 0.036 |
| 4 | ketamine 10 mg/kg | 10 | 194.5 | 86.0 | 40.3 | 15.6 | control | 0.709 | 0.477 |
| | Effect of competitive and non-competitive NMDAR antagonists in combination with selective 5-HT2A antagonist | | | | | | | | |
| 5 | MDL100907 .3 mg/kg alone | 50 | 114.3 | 129.0 | 19.2 | 20.2 | control | 0.036 | <.001 |
| 6 | MDL100907 .3 mg/kg + DCS 30 mg/kg. | 10 | 295.8 | 104.6 | 20.8 | 24.2 | MDL alone | 0.770 | 0.830 |

TABLE 1-continued

Effect of specified agents on performance in the elevated plus maze

| Line | Condition | N | Distance Traveled Open (DTO) Mean | Std dev | Percent open (PCT) Mean | Std dev | Statistical effects (p values) vs. Comparator | DTO | PCT |
|---|---|---|---|---|---|---|---|---|---|
| 7 | MDL100907 .3 mg/kg + DCS 300 mg/kg. | 10 | 261.3 | 229.3 | 35.8 | 29.2 | MDL alone | 0.006 | 0.032 |
| 8 | MDL100907 .3 mg/kg + PCP 1 mg/kg | 10 | 94.5 | 99.4 | 14.9 | 13.7 | MDL alone | 0.650 | 0.520 |
| 9 | MDL100907 .3 mg/kg + ketamine 10 mg/kg | 10 | 58.3 | 49.8 | 16.3 | 15.7 | MDL alone | 0.180 | 0.662 |

TABLE 2

Effect of DCS (300 mg/kg) in combination with SDA-type atypical antipsychotics

| Line | Condition | N | DTO Mean | Std dev | PCT Mean | Std dev | Statistical effects (p values) vs. Comparator | DTO | PCT |
|---|---|---|---|---|---|---|---|---|---|
| 1 | Lurasidone .1 mg/kg | 20 | 172.9 | 95.9 | 32.5 | 16.0 | Control | 0.660 | 0.340 |
| 2 | Lurasidone .1 mg/kg + DCS 300 mg/kg | 20 | 364.1 | 158.5 | 53.2 | 17.2 | Lurasidone .1 mg/kg | <.001 | <.001 |
| 3 | Lurasidone .2 mg/kg | 10 | 120.8 | 76.7 | 22.9 | 13.5 | Control | 0.039 | 0.013 |
| 4 | Lurasidone .2 mg/kg + DCS 300 mg/kg | 10 | 391.6 | 183.9 | 54.3 | 18.3 | Lurasidone .2 mg/kg | <.001 | <.001 |
| 5 | Lurasidone .3 mg/kg | 10 | 134.2 | 65.6 | 26.6 | 10.7 | Control | 0.097 | 0.062 |
| 6 | Lurasidone .3 mg/kg + DCS 300 mg/kg | 10 | 392.6 | 194.6 | 56.8 | 20.2 | Lurasidone .3 mg/kg | <.001 | <.001 |
| 7 | Quetiapine 30 mg/kg | 10 | 42.8 | 49.6 | 9.0 | 10.7 | Control | <.001 | <.001 |
| 8 | Quetiapine 30 mg/kg + DCS 300 mg/kg | 10 | 153.1 | 196.7 | 26.0 | 29.0 | Quetiapine 30 mg/kg | 0.100 | 0.098 |
| 9 | Aripiprazole 1 mg/kg | 10 | 113.9 | 56.9 | 34.9 | 15.5 | Control | 0.019 | 0.770 |
| 10 | Aripiprazole 1 mg/kg + DCS 300 mg/kg | 10 | 158.3 | 76.0 | 39.5 | 13.0 | Aripiprazole 1 mg/kg | 0.160 | 0.480 |
| 11 | Risperidone 1 mg/kg | 10 | 0.0 | 0.0 | 0.0 | 0.0 | Control | 0.081 | 0.160 |
| 12 | Risperidone 1 mg/kg + DCS 300 mg/kg | 10 | 1.7 | 5.4 | 0.9 | 2.7 | Risperidone 1 mg/kg | 0.039 | 0.133 |
| 13 | Brexpiprazole .3 mg/kg | 10 | 131.6 | 67.6 | 28.7 | 17.0 | Control | 0.1 | 0.2 |
| 14 | Brexpiprazole .3 mg/kg + DCS 300 mg/kg | 10 | 210.9 | 89.7 | 39.2 | 12.4 | Brexpiprazole .3 mg/kg | <0.001 | 0.1 |

Effects of DCS alone and in combination with the 5-HT2A receptor antagonist MDL100907 are showing in Table 1. First, we demonstrate that D-cycloserine selectively increases % time in open arms at a dose of 300 mg/kg but not at a dose of 30 mg/kg (line 3 vs. 2)

Here, we demonstrate that the non-competitive NMDAR antagonist ketamine does not significantly alter either distance traveled in the open arm or % time in the open arm (line 4).

Here, we repeat our finding in an expanded data set that the selective 5-HT2A receptor antagonist MDL100,907 significantly reduces both distance travelled in the open arm and % open arm activity, demonstrating increased akathisia/anxiety (Line 5).

Here we repeat our demonstration that D-cycloserine significantly reverses the effects of MDL100,907 at a dose of 300 mg/kg, but not 30 mg/kg (lines 6,7).

Here we further demonstrated that two non-competitive NMDAR antagonists, PCP and ketamine, did not significantly affect open arm behavior (lines 8,9). Moreover, these agents reduced total distance travelled suggesting general sedative effects instead of specific anti-akathisia effects.

Effects of specific atypical antipsychotics are shown in Table 2. Here we show that lurasidone at doses between 0.1-0.3 mg/kg produces a dose-dependent reduction in distance traveled in the open arm (DTO) and in % time in the open arm (PCT), with maximal effect at 0.2 mg/kg (lines 1, 3, 5). Here we show that D-cycloserine at a dose of 300 mg/kg significantly reverses the effects of lurasidone (lines 2, 4, 6).

Here we show that quetiapine produced similar results to lurasidone. These results were reversed at trend level by D-cycloserine (lines 7,8).

Here we show that aripiprazole significantly decreased distance travelled in the open arm, but not % of time in the open arm, and that D-cycloserine had no significant effect in the presence of aripiprazole (lines 11,12).

Overall, these findings demonstrate that D-cycloserine is effective in reversing akathisia (and therefore suicidality) induced by selective 5-HT2A receptor antagonists or with SDA-type atypical antipsychotics. The effectiveness is observed at a dose of 300 mg/kg, but not at a dose of 30 mg/kg.

Overall, these findings demonstrate preferential effects of D-cycloserine in reversing behavioral effects induced by lurasidone, supporting use of combined D-cycloserine and lurasidone treatment for use in psychiatric disorders including depression and schizophrenia.

SUMMARY

These findings demonstrate an unexpected ability of D-cycloserine, at high doses (i.e. when producing a net NMDAR antagonist effect), to reverse reductions in % time spent and distance travelled in the open arm of the elevated plus maze induced by 5-HT2A antagonists such as MDL100709, ketanserin or atypical antipsychotics, including lurasidone. Pro-therapeutic effects were seen not only for D-cycloserine, but also for other NMDAR antagonists such as D-CPPene, CGS19755 or CP101606. In contrast, the traditional channel blocker PCP worsened performance relative to DCS, suggesting that agents working at the glutamate or glycine binding sites, or lower affinity channel blockers, such as GlyX-13, may be superior to higher affinity non-competitive antagonists such as PCP or MK-801. Furthermore, although 5-HT2A antagonists are known to reverse hyperactivity induced by NMDA channel blockers such as ketamine, MK-801, or PCP, the % open arm measure (which compares distance travelled in open vs. closed arms) corrects for overall changes in activity levels.

These findings demonstrate that D-cycloserine unexpectedly reverses activity selectively at a net antagonistic dose of 300 mg/kg, but not at a dose of 30 mg/kg.

Response varied across atypical antipsychotics. Unexpectedly superior effects were observed with D-cycloserine in combination with the atypical antipsychotics lurasidone, risperidone and brexpiprazole.

Example 2: Effects of NMDAR Antagonists Alone and Combined with Antipsychotics and Antidepressants in the Rodent Forced Swim Test For this study, anti-depressant effects of NMDAR antagonists were assessed using the rodent forced swim tests. NMDAR antagonists were studied alone and in combination with specific 5-HT2A receptor antagonists.

All testing was performed at PsychoGenics Inc, 765 Old Saw Mill River Road, Tarrytown, N.Y. 10591, USA Male BalbC/J mice (8 weeks old) from Jackson Laboratories (Bar Harbor, Me.) were used. Upon receipt, mice were assigned unique identification numbers (tail marked) and were group housed in OPTImice cages. All animals were acclimated to the colony room for 1 week prior to testing. During the period of acclimation, animals were examined on a regular basis, handled, and weighed to assure adequate health and suitability. Animals were maintained on a 12/12 light/dark cycle. The room temperature was maintained between 20 and 23° C. with a relative humidity maintained between 30% and 70%. Chow and water were provided ad libitum for the duration of the study. All testing was performed during the animal's light cycle phase.

Mice were acclimated to the test room at least 1 hour prior to commencing the test. The forced swimming test consisted of one 6-minute session of forced swimming in individual opaque cylinders (15 cm tall×10 cm wide, 1000 ml beakers) containing fresh tap water at a temperature of 23±2° C. and a depth of 12 cm (approximately 800 ml) for each test animal. The time the animal spent immobile was recorded over the 6 min trial. Every 1 min the cumulative immobility time was recorded from the start of the session and noted on the study data record sheet. Immobility was defined as the postural position of floating in the water. The animals were generally observed with the back slightly hunched and the head above water with no movements or with small stabilizing movements of the limbs. After the swim test, each animal was placed in a pre-heated cage with a heating pad and allowed to dry.

The main variable used to represent immobility in this test was the total time immobile during the 6-min test period. Statistics were performed by analysis of variance (ANOVA) with Dunnett post-hoc testing vs. the control condition or by t-test as appropriate.

Figure 2:
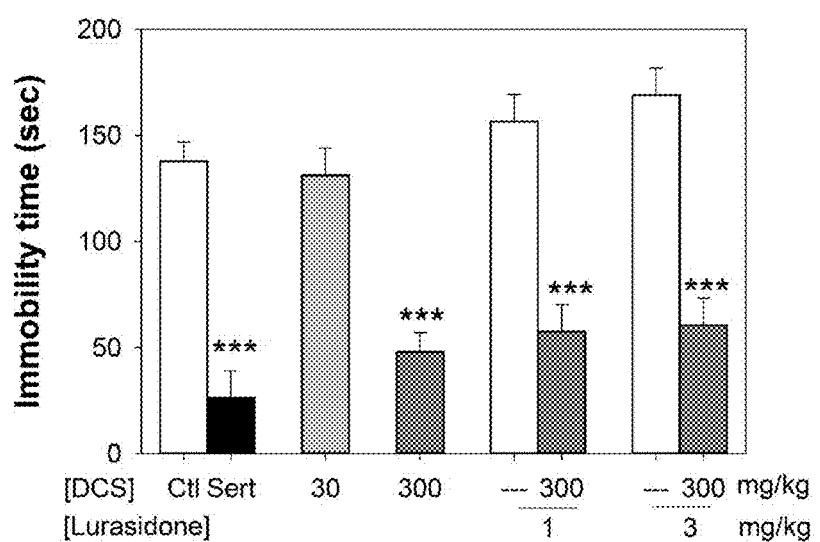
FIG. 2 shows the effects of D-cycloserine (DCS) on immobility time in the forced swim test (FST) following intraperitoneal (IP) administration in both the absence and presence of lurasidone. Between 10 and 50 mice were treated with either control (vehicle), sertraline (20 mg/kg), lurasidone (1 and 3 mg/kg) or D-cycloserine (30-1000 mg/kg). ***$p<0.001$ vs. control. The main variable used to represent immobility in this test was the total time immobile during the 6-min test period. Statistics were performed by analysis of variance (ANOVA) with Dunnett post-hoc testing vs. the control condition or by t-test as appropriate.

In one set of studies, shown in FIGS. 1 and 2, effects of D-cycloserine were investigated following either oral (PO) or intraperitoneal (IP) dosing. Sertraline, a known antidepressant, is used as a positive control.

In a second set of studies, shown in Table 3, effects of D-cycloserine were investigated in combination with antipsychotic and/or antidepressant medication.

As shown in FIGS. 1 and 2, D-cycloserine (DCS) had no significant effect in the forced swim test assay at a dose of 30 mg/kg following either IP or PO administration. During oral dosing, Also shown, D-cycloserine (DCS) produced a highly significant (p<0.001) when administered at doses of 100 mg/kg or above following either PO or IP administration.

TABLE 3

Effects of indicated antipsychotic (AP) and anti-depressant (AD) medications on immobility time (min) in the rodent forced swim test (FST) alone and in combination with D-cycloserine (DCS) at indicated doses, shown in mg/kg (mpk)

| Condition | N | Mean | Std Dev | Std. Error | P vs. control | p vs. AP/AD alone |
|---|---|---|---|---|---|---|
| Control | 50 | 128.76 | 44.33 | 6.27 | | |
| Lurasidone .2 mpk | 10 | 146.3 | 42.4 | 13.4 | | |
| Lurasidone .2 mpk + DCS 30 mpk | 10 | 129.8 | 56.0 | 17.7 | 1.000 | 0.47 |
| Lurasidone .2 mpk + DCS 300 mpk | 10 | 33.4 | 33.3 | 10.5 | 0.000 | <.001 |
| Lurasidone 1 mpk | 10 | 156.6 | 54.7 | 17.3 | 0.710 | |
| Lurasidone 1 mpk + DCS 300 mpk | 10 | 57.5 | 35.7 | 11.3 | 0.000 | <.001 |
| Lurasidone 3 mpk | 10 | 169.1 | 36.6 | 11.6 | 0.127 | |
| Lurasidone 3 mpk + DCS 300 mpk | 10 | 60.5 | 33.4 | 10.6 | <.001 | <.001 |
| Brexipiprazole .3 mpk | 10 | 238.8 | 28.8 | 9.1 | <.001 | |
| Brexipiprazole .3 mpk + DCS 300 mpk | 10 | 197.2 | 42.8 | 13.5 | <.001 | 0.02 |

As shown in Table 3, lurasidone alone did not significantly affect immobility in the forced swim test. Similarly, D-cycloserine (DCS) did not significantly reduce immobility in the forced swim test when administered at a dose of 30 mg/kg in combination with lurasidone. In contrast, D-cycloserine (DCS) significantly reduced immobility in the forced swim test when administered at a net antagonist dose of 300 mg/kg in combination with lurasidone administered at dose of 0.2 to 3 mg/kg. Likewise, D-cycloserine (DCS) significantly reduced immobility in the forced swim test when administered at a dose of 300 mg/kg in combination with the compound brexpiprazole. As shown in the table, Brexipiparazole on its own significantly increased immobility. DCS significantly reversed this increase.

Also as shown in Table 3, D-cycloserine (DCS) did not significantly reduce immobility in the forced swim test when administered at a dose of 300 mg/kg in combination with aripiprazole.

Together, the findings presented in Table 3 demonstrate that D-cycloserine, when administered at a net NMDAR antagonistic dose produces significant antidepressant effects that are synergistic with known antidepressant and antipsychotic agents, and moreover, that D-cycloserine produces unexpectedly superior beneficial effects in combination with the compounds lurasidone and bexpiprazole. These findings also demonstrate that the anti-depressant effects of D-cycloserine unexpectedly occurs only at doses of 300 mg/kg or greater.

Example 3: Pharmacokinetics of D-Cycloserine in Rodents

For this study, the pharmacokinetics of D-cycloserine in rodents were assessed. This study tests the hypothesis that anti-akathisia and antidepressant effects of DCS presented in the above examples are observed specifically at treatment levels that produce sustained blood DCS levels of >25 microgram/mL.

For this study, male C57BL/6J mice (8 weeks old) from Jackson Laboratories (Bar Harbor, Me.) were used. D-cycloserine (30, 100, 300, 500 and 1000 mg/kg) was dissolved in PTS vehicle (5% PEG200: 5% Tween80: 90% NaCl) and administered IP at a dose volume of 10 mL/kg.

For each treatment group a total of 12 mice were dosed: 4 mice were collected at 30, 60 and 120 min. Mean plasma level was computed over this time period. Analysis of DCS in plasma was performed utilizing an UPLC/MS/MS system consisted of an Acquity UPLC chromatographic system and a Quattro Premier XE triple quad mass spectrometer, both from Waters. Isolation of DCS was achieved using a 5 minute (total run time) HILIC methodology which provided an LLOQ of 5 ng/mL.

Results of the experiment are shown in Table 4.

Figure 3:
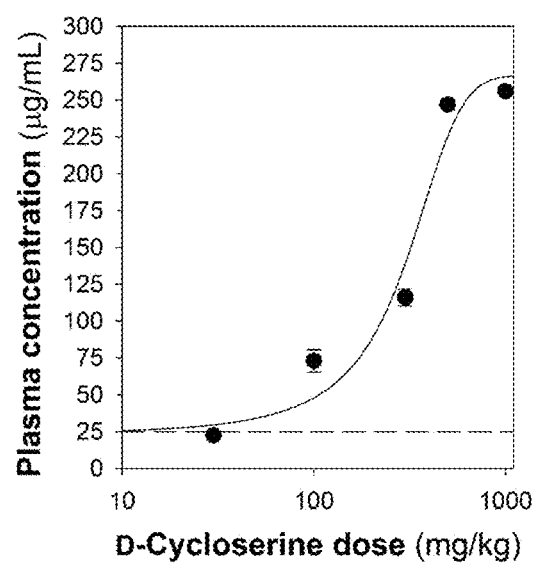
FIG. 3 shows the pharmacokinetics of DCS in rodent. 8 mice were treated with DCS at 30, 100, 300, 500 and 1000 mg/kg which was administered by IP in order to determine what dose produces and effect of DCS plasma levels of >25 microgram/mL. Shown on the graph is plasma (±sem) DCS level vs. dose.

As shown in FIG. 3, peripheral D-cycloserine administration was associated with a dose-dependent increase in plasma D-cycloserine over the 30-120 min (p<0.0001). Plasma levels associated with 30 mg/kg DCS treatment were associated with mean plasma levels below 25 microgram/mL. Plasma levels associated with doses of 100 mg/kg or above were all significantly greater than 25 microgram/mL. The maximum tolerated dose was 500-1000 mg/kg, suggesting a maximum tolerated blood level of approximately 125 ug/mL.

Example 4: Benefits of Protection of D-Cycloserine from Gastric Degradation

Because of its chemical structure, D-cycloserine is susceptible to hydrolysis in aqueous solution under acidic (low pH) conditions, such as may be observed in the stomach, as described by Malspeis and Gold, J Pharmaceutical Sci, 53:113-80, 1964, among others.

Gastric emptying may persist for up to 3 hours, permitting time for hydrolysis of up to 50% of orally administered D-cycloserine.

Enteric coating and prodrug manufacture are known to decrease sensitivity of medications to hydrolysis in the stomach. Examples of prodrugs are described in Fedor et al., Int J Pharmaceutics 22:197-205, 1984, among others. Reduction of hydrolysis by enteric coating or by manufacture of a hydrolysis-resistant prodrug would decrease the oral dose of D-cycloserine needed to achieve the desired plasma levels of >25 microgram/mL.

Effects of different levels of protection from gastric degradation are shown in Table 4, assuming 50% gastric degradation of D-cycloserine if no enteric coating or prodrug modification is present.

TABLE 4

Effects of protection against gastric degradation on D-cycloserine dose needed to obtain plasma levels in excess of 25 microgram/mL assuming 50% hydrolysis

| % Protection | Degree of hydrolysis (%) | Dose needed (mg) |
|---|---|---|
| 0 | 50 | 500 mg |
| 50 | 25 | 375 |
| 100 | 0 | 250 mg |

This analysis shows the potential benefit of formulation of D-cycloserine for sustained release and protection from gastric degradation.

Example 5: Anti-Depression Effect of NMDAR Antagonist Compounds

For this study, further NMDAR antagonist compounds were tested for their ability to reduce immobility time in the rodent FST test, indicative of potential anti-depressant effects, and further 5-HT2AR antagonists were tested for their ability to produce reductions of time spent in the open arms of the EPM, indicative to potential liability to induce anxiety, akathisia and suicidality in humans Table 5 shows data for sertraline and for the NMDAR antagonists CGS-19755, D-CPPene and Gavestinel, in the FST. As shown, both CGS-19755 and gavestinel numerically reduce immobility in the FST at indicated doses, consistent with clinical anti-depressant effect.

TABLE 5

Mean immobility time in the rodent forced swim test (FST) for the indicated compounds and doses.

| Condition | N | Mean | Std. Deviation | Std. Error | LSD |
|---|---|---|---|---|---|
| Vehicle | 10 | 159.60 | 58.002 | 18.342 | |
| Sertraline, 20 mg/kg | 10 | 85.50 | 64.400 | 20.365 | 0.003 |
| CGS-19755, 0.03 mg/kg | 10 | 125.60 | 59.176 | 18.713 | 0.161 |
| CGS-19755, 0.1 mg/kg | 10 | 144.30 | 36.755 | 11.623 | 0.528 |
| CGS19755, 0.3 mg/kg | 10 | 120.00 | 54.207 | 17.142 | 0.103 |
| CGS-19755, 1.0 mg/kg | 10 | 137.20 | 37.055 | 11.718 | 0.356 |
| CGS-19755, 3.0 mg/kg | 10 | 154.90 | 45.569 | 14.410 | 0.846 |
| CGS-19755, 10 mg/kg | 10 | 114.70 | 62.109 | 19.641 | 0.065 |
| D-CPPene, 0.03 mg/kg | 10 | 124.20 | 50.778 | 16.057 | 0.145 |
| D-CPPene, 0.1 mg/kg | 10 | 153.40 | 69.754 | 22.058 | 0.798 |
| D-CPPene, 0.3 mg/kg | 10 | 129.10 | 67.765 | 21.429 | 0.209 |
| D-CPPene, 1.0 mg/kg | 10 | 156.80 | 54.358 | 17.190 | 0.908 |
| D-CPPene, 3.0 mg/kg | 10 | 124.60 | 81.508 | 25.775 | 0.150 |
| D-CPPene, 10 mg/kg | 10 | 141.20 | 47.112 | 14.898 | 0.448 |
| Gavestinel (0.1 mg/kg) | 10 | 136.10 | 39.776 | 12.578 | 0.333 |
| Gavestinel, 0.3 mg/kg | 10 | 116.30 | 38.563 | 12.195 | 0.075 |
| Gavestinel, 1.0 mg/kg | 10 | 109.60 | 45.471 | 14.379 | 0.040 |
| Gavestinel, 3 mg/kg | 10 | 122.70 | 43.673 | 13.811 | 0.129 |
| Gavestinel, 10 mg/kg | 10 | 111.40 | 59.943 | 18.956 | 0.048 |
| Gavestinel, 30 mg/kg | 10 | 131.90 | 37.242 | 11.777 | 0.254 |

Table 6 shows Distance travelled in the open arm of the EPM test for the indicated compounds, along with statistical analysis. As can be appreciated, the selective 5-HT2AR antagonists SR46349B, EMD281014, and Pimavanserin significantly reduced distance travelled in the open arm relative to the vehicle (DOI, (2 mg/kg) was added in all conditions). Significant effects were also observed for the atypical antipsychotics cariprazine, risperidone, and brexpiprazole, which may be effective in the treatment of treatment-resistant major depressive disorder. By contrast, no significant effects were observed for the anti-depressant compounds venflaxine, fluoxetine, imipramine, vortioxetine, or levomilnacipran.

These findings demonstrate potential therapeutic utility of NMDAR antagonists acting through the glutamate or glycine binding sites in treatment of depression and suicidality, and of synergistic interactions between NMDAR antagonists and atypical antipsychotics used to treat major depressive disorder.

TABLE 6

Mean distance travelled in the open arm of the EPM for the indicated compounds and doses.

| Condition | N | mean | std | ste | p vs. vehicle |
|---|---|---|---|---|---|
| Vehicle alone | 14 | 264.57 | 112.126 | 29.967 | |
| D-cycloserine, 300 mg/kg | 10 | 369.70 | 146.083 | 46.195 | 0.01619 |
| SR46349B, 0.3 mg/kg | 10 | 127.10 | 58.118 | 18.378 | 0.00175 |
| SR46349B, 1.0 mg/kg | 10 | 98.00 | 75.048 | 23.732 | 0.00016 |
| SR46349B, 10 mg/kg | 10 | 105.90 | 106.325 | 33.623 | 0.00032 |

TABLE 6-continued

Mean distance travelled in the open arm of the EPM for the indicated compounds and doses.

| Condition | N | mean | std | ste | p vs. vehicle |
|---|---|---|---|---|---|
| EMD281014, 1 mg/kg | 10 | 111.00 | 103.751 | 32.809 | 0.00049 |
| EMD281014, 3 mg/kg | 10 | 42.70 | 42.529 | 13.449 | 0.00000 |
| END281014, 10 mg/kg | 10 | 44.80 | 29.914 | 9.460 | 0.00000 |
| Pimavanserin, 0.3 mg/kg | 10 | 150.20 | 92.061 | 29.112 | 0.00897 |
| Pimavanserin, 1.0 mg/kg | 10 | 204.10 | 146.281 | 46.258 | 0.16477 |
| Pimavanserin, 10 mg/kg | 10 | 66.50 | 112.811 | 35.674 | 0.00001 |
| Cariprazine, 0.03 mg/kg | 10 | 186.00 | 123.755 | 39.135 | 0.07149 |
| Cariprazine, 0.1 mg/kg | 10 | 174.30 | 83.371 | 26.364 | 0.03861 |
| Cariprazine, 1 mg/kg | 10 | 69.70 | 58.511 | 18.503 | 0.00001 |
| Risperidone, 1 mg/kg | 10 | 5.30 | 16.760 | 5.300 | 0.00000 |
| Venflaxine, 40 mg/kg | 10 | 224.60 | 215.474 | 68.139 | 0.35790 |
| Fluoxetine, 10 mg/kg | 10 | 216.70 | 100.981 | 31.933 | 0.27106 |
| Imipramine, 10 mg/kg | 10 | 235.00 | 143.029 | 45.230 | 0.49622 |
| Vortioxetine, 10 mg/kg | 10 | 237.90 | 117.300 | 37.093 | 0.53936 |
| Levomilnacipran, 40 mg/kg | 10 | 237.90 | 97.789 | 30.924 | 0.53936 |
| Brexpiprazole, 0.1 mg/kg | 10 | 160.10 | 83.734 | 26.479 | 0.01686 |
| Brexpiprazole, 0.3 mg/kg | 10 | 204.70 | 96.663 | 30.568 | 0.16898 |
| Brexpiprazole, 1 mg/kg | 10 | 93.70 | 40.461 | 12.795 | 0.00011 |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A method for treating a subject with depression or suicidality and in need of treatment with an atypical antipsychotic, but in need of reduced side effects thereof, the method comprising:
   administering to the subject an atypical antipsychotic that is a combined dopamine D2/5-HT2A receptor antagonist in a composition comprising
   an NMDAR-antagonist effective amount of D-cycloserine; and
   an effective amount of an atypical antipsychotic that is a combined dopamine D2/5-HT2A receptor antagonist,
   wherein the NMDAR-antagonist effective amount of D-cycloserine is sufficient to produce a sustained blood plasma concentration in excess of 25 microgram/mL but lower than 125 microgram/mL, and
   wherein the atypical antipsychotic is lurasidone, and wherein the effective amount of the lurasidone is between 20 mg-200 mg per day,
   thereby treating the subject with the atypical antipsychotic, but with reduced side effects.

2. The method of claim 1, wherein the NMDAR-antagonist effective amount of D-cycloserine is in excess of 500 mg/day and less than 1000 mg.

3. The method of claim 1, wherein the NMDAR antagonist effective amount of D-cycloserine is in excess of 10 mg/kg/day, and is less than 25 mg/kg/d.

4. The method of claim 1, wherein the pharmaceutical composition is formulated for sustained release.

5. The method of claim 1, wherein the composition further comprises an enteric coating.

6. The method of claim 1, wherein the NMDAR-antagonist effective amount of D-cycloserine is provided as a prodrug.

7. The method of claim 1, wherein the side effects are at least one anxiogenic side effect.

8. The method of claim 1, wherein the at least one anxiogenic side effect is selected from the group consisting of akathisia, agitation, anxiety, and suicidality.

9. The method of claim 1, wherein the depression is major depression or bipolar depression.

\* \* \* \* \*